April 1, 1947. M. A. DAUERNHEIM Plant Pat. 734
AZALEA PLANT
Filed March 7, 1946
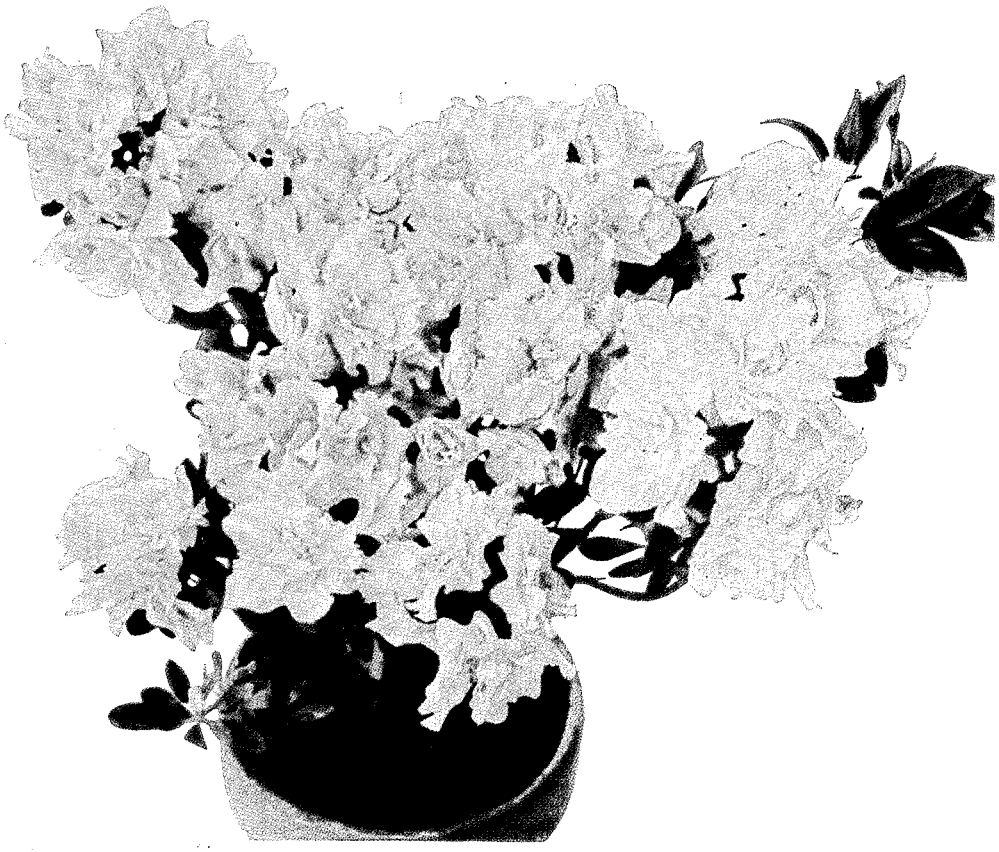
Inventor
M. A. Dauernheim
By Robb & Robb
attorneys Patented Apr. 1, 1947

Plant Pat. 734

UNITED STATES PATENT OFFICE

734

AZALEA PLANT

Mel A. Dauernheim, Wantagh, N. Y., assignor to Dauernheim, Inc., Wantagh, N. Y., a corporation of New York Application March 7, 1946, Serial No. 652,595

1 Claim. (Cl. 47—60)

The present discovery relates to a new and distinct variety of azalea plant, originating as a sport of "Mme. Pericat," a well-known variety of Kurume class.

This new azalea is of such a distinctive character as to make it difficult to compare it with any other Kurume, even its parent plant. While it has the same growing habit, as regards vigor and general branching habit of its parent "Mme. Pericat," yet it differs therefrom and all others dominantly, in that the color of the flowers is different, the flowers are more wavy and the foliage is quite distinct because said foliage is pointed, at least as far as the larger leaves are concerned. The color of the bloom is very pleasing and excellent in quality, and the plant, when in any stage of bloom, furnishes a mass of color having little or no distracting shades.

The bud formation of this new variety is similar to the variety "Sweetheart Supreme," and is very desirable from that standpoint alone. The vigorous habit of the plant is easily controlled, and this, with the soft color of the flowers and its best flowering period, conduces to make this plant most desirable for the public demand over an extended period from about the middle of February through Easter.

Perhaps one of the most important and distinctive features of the flowers resides in the formation of the petals, so-called, which are of the hose-in-hose type, having two star-shaped layers, with a cluster of petaloids in the center, irregularly shaped and pointing outward, thus giving to each bloom the appearance of doubleness.

Asexual reproduction of this new variety shows the foregoing characteristics come true to form and are established.

The drawing illustrates a potted plant of this new variety in bloom and plainly discloses the double appearance of the blossoms as well as the density of the mass due to the large cluster groups.

The following is a detailed description of the new variety, color terminology being in accord with the ordinary dictionary definition, except where indicated to be in accordance with the R. F. Wilson's Horticultural Colour Chart:

Propagation: Holds its distinguishing characteristics through succeeding propagations by cuttings.

Growth habit: Vigorous, similar to "Mme. Pericat."

Rooting: Easy rooting.

Blooming habit: Under conditions prevailing in Long Island blooms evenly as most all other azalea varieties which are grown, if flowered at proper season.

Blooming season: As this is a semi-hardy variety, it is difficult to determine exactly when it would bloom naturally. This and similar varieties are carried through their dormancy with protection. Older plants (two-year old and older) may be carried through the winter in cold frames and in the location of Long Island bloom about May 5–15.

*Suitability for forcing.*—May be forced in good condition from February 1–May 1, and therefore suitable for Easter demand.

Foliage:

*Size.*—Large for Kurume type. The mature foliage of the strongest branches are from 1¼ to 1¾ inches long. If plants are not pinched often and growth is consequently more straggly, foliage may be larger.

*Quantity.*—Normal.

*Color.*—*New foliage*—upper side—lighter than upper side of old foliage; under side—lighter than upper side of old foliage. *Old foliage*—upper side—Parsley Green, Plate 00962, page 193; under side—lighter than upper side.

*Shape.*—Oval pointed.

*Appearance.*—Upper side—glossy but not smooth; under side—slightly rough.

*Edge or margin.*—Smooth.

*Disease resistance.*—Good.

*Flower*

Locality where specimens described were grown: Wantagh, Long Island, New York.

Flowers borne: Three to seven or more to a stem. The tallest and strongest stems form the largest and fullest clusters.

Quantity of bloom: Free and abundant in greenhouse.

Continuity: One crop per season. Similar to all other varieties of azaleas which are grown under similar conditions.

Petalage: A hose-in-hose type with two layers star-shaped, with an additional cluster of petaloids in the center irregularly shaped and pointed outward giving the appearance of doubleness.

*Color.*—Rhodonite Red, Plate 0022/1, page 188.

*Texture.*—Slightly velvety.

*Appearance.*—Even distribution of color with a slight mottling of Magenta spots, but which do not detract appreciably from general color. The upper and bottom layer of petals are five-pointed and the upper layer is the largest. The bottom layer is slightly smaller, the points of which bisect those of the upper layer. The central group of petaloids is smaller than the others and, instead of having a similar star formation, is somewhat irregular and pointing outward to give a double appearance. The entire flower is slightly ruffled. The blooms vary from 1½ to 2¼ inches in diameter.

*Outside.*—The color of the outer side of the flower is similar to that of the inside, shading only slightly lighter towards the base. In general appearance of the plant in bloom, it is a mass of color of one shade.

Bud: Similar in form to azalea "Sweetheart Supreme" (similar to the bud formation of a "Sweetheart" rose). The bud is more open and not pointed as most varieties of Kurumes. The color of the buds, when half open, is similar to the color of the open flower. In tighter buds, there may be a slightly lighter shade along the center of each petal.

Reproductive organs:

*Stamens.*—Color—Brown with stem similar in color to the rest of the flower. Anthers are on stamens and some of the anthers are on the petaloids.

*Pollen.*—Light Green.

*Styles.*—Similar in color to the rest of the flower.

I claim:

A new and distinct variety of azalea plant, characterized as to novelty by the color and form of its flowers, which include a cluster of irregular, erect petaloids in the center giving the appearance of doubleness; the form of the buds; and the pointed form of the mature foilage, substantially as shown and described.

MEL A. DAUERNHEIM.